United States Patent [19]

Scott

[11] Patent Number: 5,046,487

[45] Date of Patent: Sep. 10, 1991

[54] THERAPEUTIC LEG ELEVATOR

[76] Inventor: James W. Scott, 403 W. 16th St., Tifton, Ga. 31794

[21] Appl. No.: 448,834

[22] Filed: Dec. 12, 1989

[51] Int. Cl.[5] .......................... A61F 5/04; A47C 20/00; A47C 16/00

[52] U.S. Cl. .......................................... 128/25 B; 5/443; 5/431; 297/439; 128/87 R; 128/89 R; 128/80 R; 128/DIG. 15

[58] Field of Search ...................... 128/25 R, 25 B, 68, 128/69, 82, 87 R, 89 R, 94, 845, 869, 882, 876, 877, DIG. 15; 272/96; 5/431, 443, 444; 297/438, 439

[56] References Cited

U.S. PATENT DOCUMENTS

| | | | |
|---|---|---|---|
| 3,430,956 | 3/1969 | Borgeas | 272/96 |
| 3,857,390 | 12/1974 | Hanson | 5/443 |
| 3,903,878 | 9/1975 | Spann | 128/DIG. 15 |
| 4,286,588 | 9/1981 | Lovegrove | 128/DIG. 15 |
| 4,323,060 | 4/1982 | Pecheux | 128/25 R X |
| 4,336,796 | 6/1982 | Andrews et al. | 128/87 R |
| 4,566,449 | 1/1986 | Smith | 128/845 |
| 4,699,130 | 10/1987 | Hossler | 128/89 R |

FOREIGN PATENT DOCUMENTS

| | | | |
|---|---|---|---|
| 1129228 | 1/1957 | France | 128/82 |
| 447474 | 3/1968 | Switzerland | 128/93 |

OTHER PUBLICATIONS

Advertisement–"Comfort Wedge," Comfort Products, Hayward, CA, 1981.

*Primary Examiner*—Richard J. Apley
*Assistant Examiner*—Karen G. Horowitz
*Attorney, Agent, or Firm*—Bradford E. Kile

[57] ABSTRACT

A therapeutic leg elevator for promoting venous flow during patient recuperation including a substantially homogeneous solid polygonal shaped member having at least one inclined surface for supporting a back portion of a patient's thigh and second inclined surface with respect to the first for supporting the patient's lower leg, a member is releasably connected to a distal end of the homogeneous support member to provide resistance exercise for the patient.

18 Claims, 2 Drawing Sheets

FIG. 1
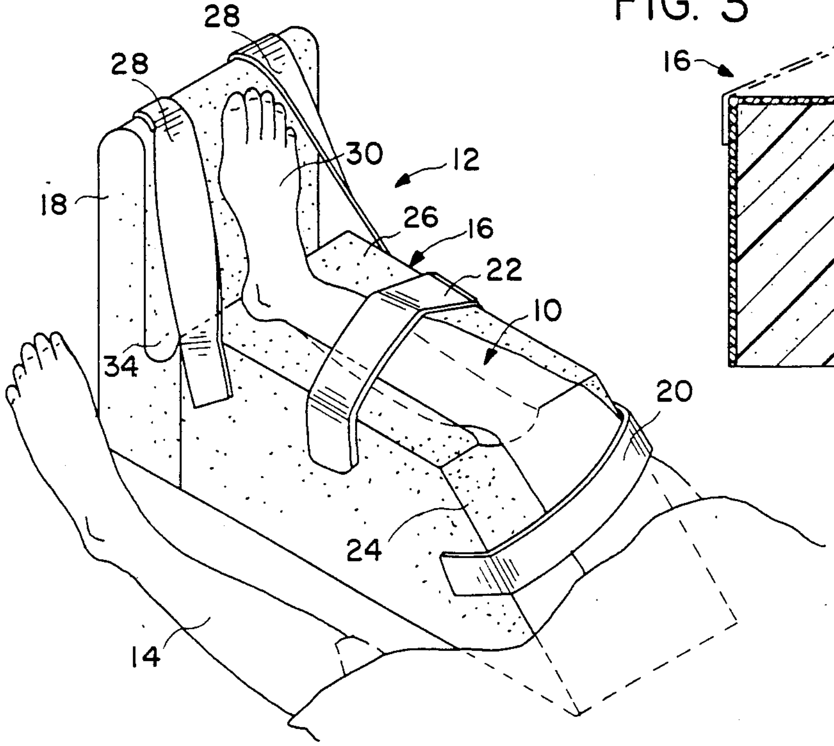
FIG. 3
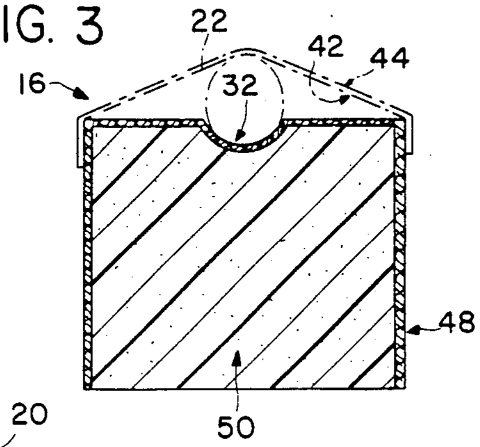
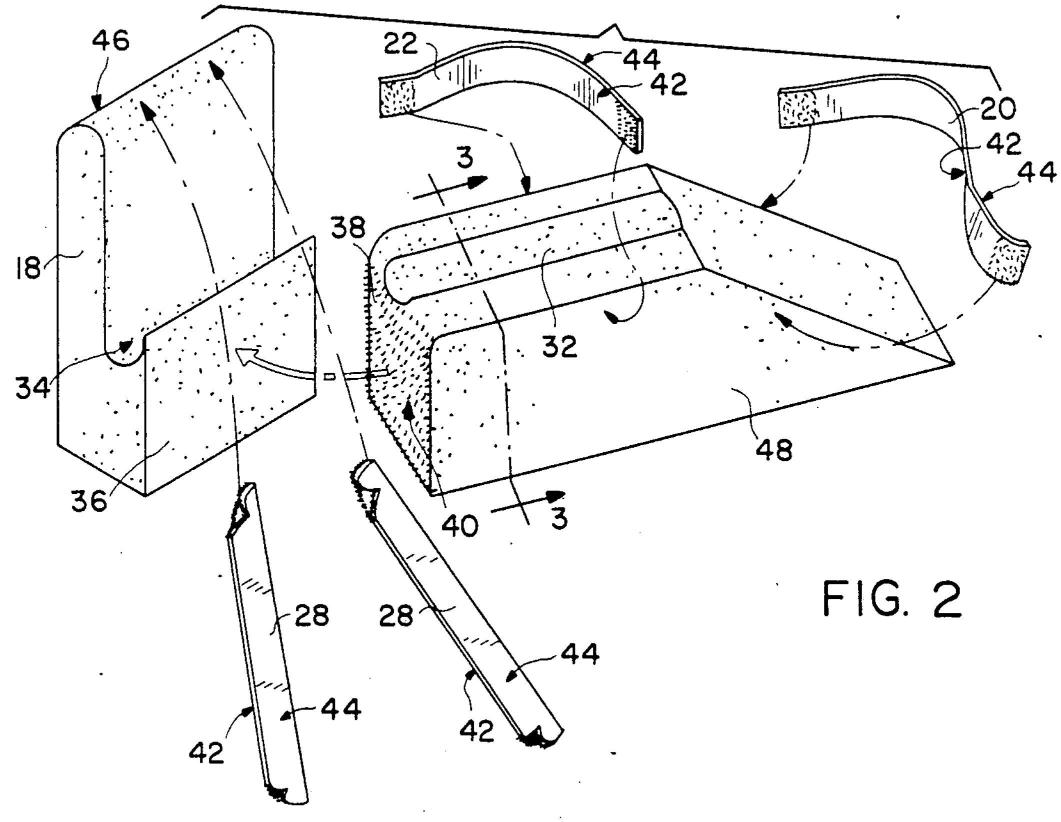
FIG. 2

THERAPEUTIC LEG ELEVATOR

BACKGROUND OF THE INVENTION

This invention relates to a novel therapeutic leg elevator for use following surgery. More specifically, this invention relates to a therapeutic leg elevator for use in promoting venous flow during post-operative patient recuperation.

Subsequent to leg or hip surgery, a patient is usually confined to a bed in a recuperative supine position. During such recovery, swelling and the absence of muscle contractions, etc. tends to inhibit the return flow of blood from the lower extremities of the leg. For example, surgery performed upon the knee complicates return to the heart of blood from the foot. The accumulation of excess fluid, known as edema, in the foot is a result of a higher osmotic pressure in the tissues surrounding the veins than in the veins themselves. Obstruction to tibial venous flow, for example adjacent the knee, results in edema by the mechanical factor of increased pressure in the capillaries of the foot. The excess fluid causes additional swelling, which is uncomfortable for the patient, and may lead to another undesirable condition known as venous stasis. The slowing of circulation of the blood, or venous stasis, may lead to venous thrombosis. Venous thrombosis may result in vein occlusion and possible pulmonary emboli, or clots to the lung, which are potentially fatal. Inhibition of circulation also tends to retard convalescence of the operative portion of the leg or hip.

It is therefore highly desirable to promote and facilitate venous outflow from the lower extremities of the leg. This may be accomplished by physical, versus prescriptive, means. Two physical means by which venous outflow can be enhanced are exercise and elevation of the lower extremity of the leg above the heart. During exercise, the calf muscle reduces venous pressure in the deep veins by emptying them and when the muscle relaxes, the superficial veins drain into the deep system rapidly. The ability to move large volumes of blood during the hyperemia of exercise prevents edema formation by maintaining a normal pressure gradient across the capillary bed. When the leg is elevated above the heart, gravity induces blood to flow away from the foot and back to the heart.

One previously known leg rest supported a patient's leg under the calf and allowed the foot to extend beyond the support. The leg rest did not, however, elevate the foot above the knee, and the potential for edema in the foot remained.

This simple configuration was then modified to include an arcuate depression in a gently sloping surface of an elevator which cradled and elevated the leg. However, the foot was still allowed to drape over the end of the elevator, contributing to problems of the type previously described.

An improved technique for elevating the leg was devised in which there were two different inclines In this configuration, the foot was elevated above the knee, and the knee was elevated above the hip. This improved the passive return of blood flow to the heart by gravity and decreased incidence of edema. Also, units have been devised in the past in which the angles of elevation could be altered for the needs of individual patients.

In yet another configuration, a heel supporting boot encompassed the lower leg from the foot to the calf and used straps across an uncovered portion of the lower leg to secure the support to the leg. The foot was in contact with the support and only the toes were exposed. This configuration did not have differentially sloping inclines; it elevated the foot relative to the knee.

An alternative arrangement to the configurations previously described is sometimes employed whereby pillows elevate the patient's knee, and multiple pillows are utilized to elevate the foot further. This arrangement, however, is not particularly stable and the pillows must be manipulated until a comfortable arrangement is found.

Passive compression has been applied to the leg by putting pneumatic tourniquets around the leg and having the tourniquets squeeze the leg to induce circulation. The action is such that by compressing the veins, blood is forced to circulate. Check valve like mechanism within the veins control the direction of blood movement so that movement in the wrong direction is not a concern. The disadvantage to using a tourniquet is that the patient must be monitored and cannot self control the frequency of compression.

The difficulties suggested in the preceding are not intended to be exhaustive but rather are among many which may tend to reduce the effectiveness of prior therapeutic post surgery leg elevators. Other noteworthy problems may also exist; however, those presented above should be sufficient to demonstrate that therapeutic leg elevators appearing in the past will admit to worthwhile improvement.

OBJECTS AND BRIEF SUMMARY OF THE INVENTION

Objects

It is therefore a general object of the invention to provide a novel therapeutic leg elevator which will obviate or minimize difficulties of the type previously described.

It is a specific object of the invention to provide a therapeutic leg elevator which may be used to facilitate lower limb venous flow during patient recuperation.

It is another specific object of the invention to provide a therapeutic leg elevator which will admit to self actuation by a patient to exercise a patient's extremity.

It is another object of the invention to provide a therapeutic leg elevator which will enhance patient comfort while stabilizing an extremity of a patient reclined in a recuperative supine position.

It is still another object of the invention to provide a therapeutic leg elevator which will elevate a patient's ankle above a patient's knee, and the knee higher than the hip, when a patient is reclined in a recuperative supine position.

It is a further object of the invention to provide a therapeutic leg elevator which operably provides adjustable resistance to be used to exercise the calf muscle of a patient in a recuperative supine position.

It is yet a further object of the invention to provide a therapeutic leg elevator which has self restoring characteristics.

It is still a further object of the invention to provide a therapeutic leg elevator which operably permits facile neurovascular examination.

It is yet another object of the invention to provide a therapeutic leg elevator which allows maximum air circulation around the recuperating leg of a patient.

It is yet still a further object of the invention to provide a therapeutic leg elevator which provides a degree of adjustability.

It is yet still another object of the invention to provide a therapeutic leg elevator which is easily manufactured, easily personalized to various sized patients, inexpensive, and thus disposable.

BRIEF SUMMARY OF A PREFERRED EMBODIMENT OF THE INVENTION

A preferred embodiment of the invention which is intended to accomplish at least some of the foregoing objects includes a substantially homogeneous solid polygonal-shaped elevating member composed of elastic foam having self restoring characteristics. The polygonal-shaped elevating member is comprised of a first inclined surface for supporting a back portion of a patient's thigh and an adjacent second inclined surface angled at a lesser degree for supporting a patient's lower leg. The second inclined surface includes an arcuate elongated groove which cradles, restrains, and receives a patient's lower leg. Lateral and distal vertical sides of the polygonal-shaped elevating member have releasably connecting hook and pile members, such as VELCRO, extending outward. The polygonal-shaped elevating member has a substantially flat bottom surface.

Elastic straps overlay the patient's upper and lower leg and are releasably attached to the sides of the polygonal-shaped elevating member by VELCRO. The elastic straps secure a patient's leg in a stable position and allow facile adjustment as necessitated by a patient.

The leg elevator permits releasable attachment of a cantilever member by means of VELCRO to the distal end of the solid. The cantilever member extends above the plane of the second inclined surface such that a patient's foot will contact the cantilever member's surface. The cantilever member provides resistance to the sole of a patient's foot and is used for dorsiflexion to stimulate venous outflow from the foot. The cantilever member is comprised of the same foam material as the polygonal-shaped elevating member and includes an elongated concave channel fashioned near a lower end of the cantilever member. The concave channel operably serves as a hinge for the resistance needed to exercise a patient's lower leg.

A pair of elastic straps are releasably connected between the superior edges of the cantilever vertical member and the lateral sides of the polygonal-shaped elevating member. These straps securely engage the cantilever member and oppose movement of the cantilever member, thereby providing resistance to the foot. In use, the elastic straps stretch so that the cantilever member bends with dorsiflexion. The straps are adjustably engaged with the lateral sides of the polygonal-shaped elevating member so that the angle between the cantilever member and the second inclined surface of the polygonal-shaped elevating member may also be variable, allowing adjustment for the needs of individual patients.

THE DRAWINGS

Other objects and advantages of the present invention will become apparent from the following detailed description of a preferred embodiment thereof taken in conjunction with the accompanying drawings, wherein:

FIG. 1 is an axonometric view disclosing the context of the subject invention and depicts the leg of a patient lying in a supine recuperative position secured to a leg elevator by elastic straps about the upper and lower leg in accordance with a preferred embodiment of the invention;

FIG. 2 is an exploded axonometric view of the subject invention illustrating the assembly of the solid polygonal elevator and the cantilever member, and accompanying positioning of the elastic straps for securing both the cantilever member to the solid polygonal elevator, and a patient's leg to the polygonal-shaped elevating member;

FIG. 3 is a cross-sectional view of the polygonal-shaped elevating member, as taken along section line 3—3 in FIG. 2, illustrating the positioning of the lower leg cradled in an elongated arcuate groove for securing the lower leg;

Figure 4:
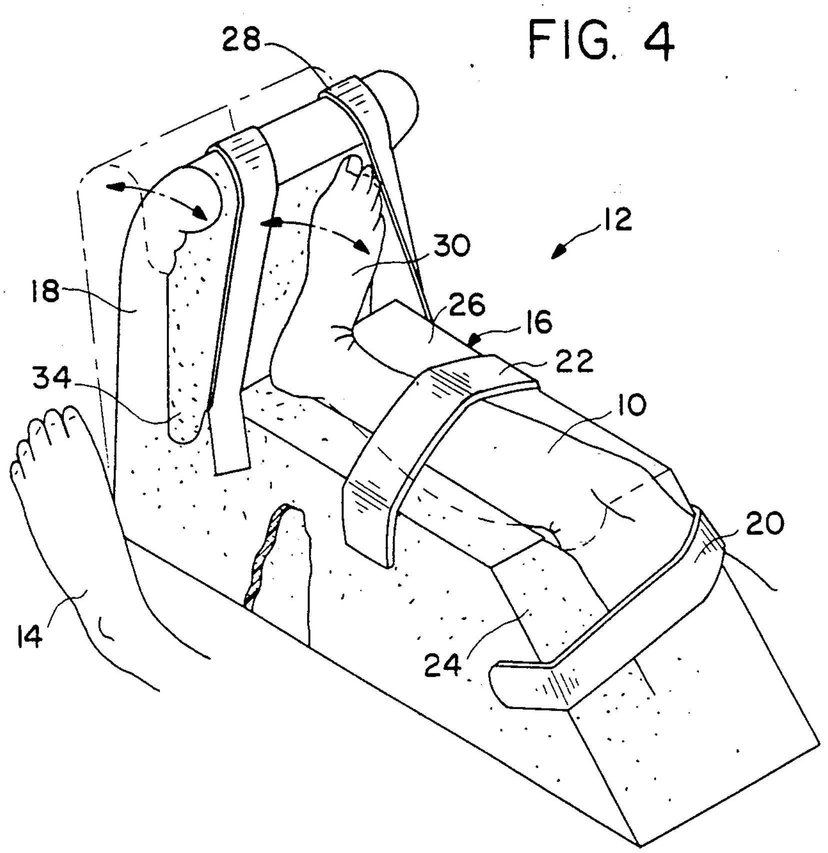
Figure 5:
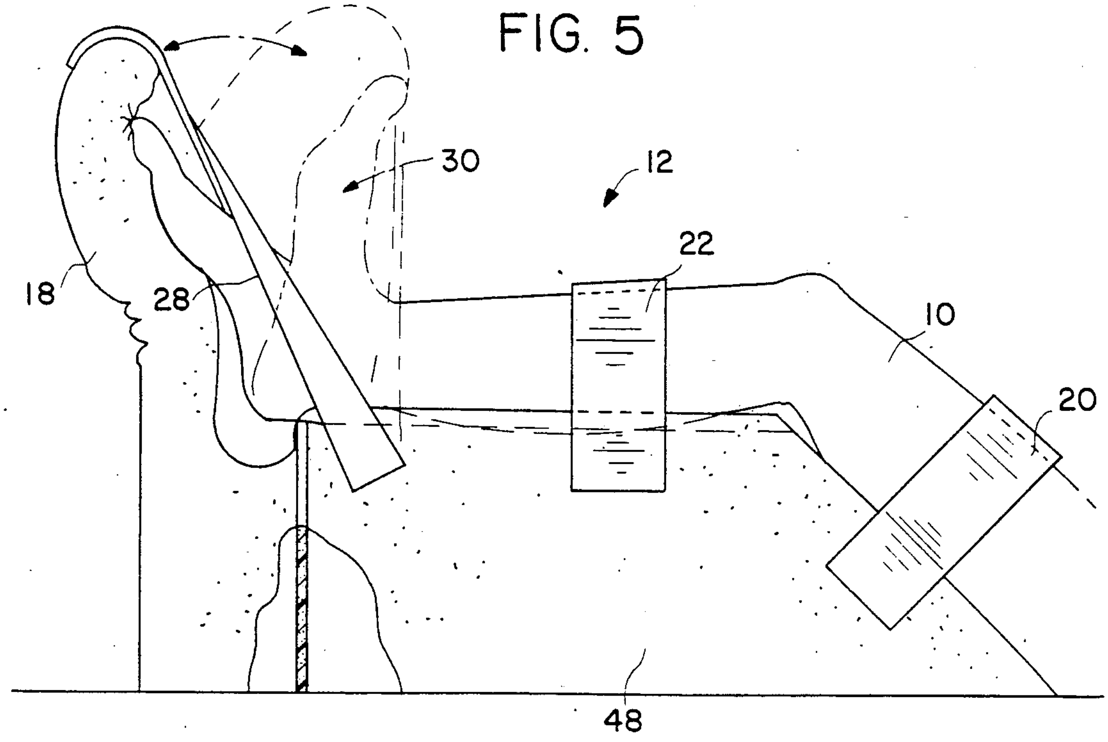

FIG. 4 is an axonometric view of the subject invention disclosing a patient's recuperating leg secured to the therapeutic leg elevator, and the range of motion of the cantilever member associated with dorsiflexion applied to the cantilever member; and FIG. 5 is a side elevational view of the subject invention illustrating the range of motion of the cantilever member which accompanies dorsiflexion of the foot while the leg is secured to the polygonal-shaped elevating member of the subject invention by elastic straps.

DETAILED DESCRIPTION

Referring now to the drawings, wherein like numerals indicate like parts, and initially to FIG. 1, there will be seen an operative context of the subject invention. More particularly, the recuperating leg 10 of a patient lying in a supine position is shown positioned in a therapeutic leg elevator 12 in accordance with a preferred embodiment of the subject invention. The patient's non recuperating leg 14 is shown laterally positioned to the therapeutic leg elevator 12 on the surface on which the patient is reclined.

The therapeutic leg elevator 12 includes a solid polygonal-shaped elevating member 16 and an attached cantilever member 18 which provides resistance for dorsiflexion. A recuperating leg 10 is secured to the polygonal-shaped elevating member 16 by a first 20 and a second 22 elastic strap. The first elastic strap 20 releasably secures an upper portion of the recuperating leg 10 to a first inclined surface 24, and the second elastic strap 22 releasably secures the lower portion of the recuperating leg 10 to a second inclined surface 26. The first inclined surface 24 of the therapeutic leg elevator 12 is inclined to a greater degree than the second inclined surface 26.

The cantilever member 18 is releasably secured to the polygonal-shaped elevating member 16 by a hook and pile connecting interforce. The cantilever member 18 provides resistance to the foot 30 of a patient such that when a patient applies pressure to the cantilever member 18, the patient's calf muscle will be exercised. In this connection elastic straps 28 extend between an upper portion of the cantilever member 18 and the polygonal-shaped elevating member 16 to provide enhanced resistance to flexion.

FIG. 2 is a more detailed view of the subject therapeutic leg elevator 12. Shown is an arcuate elongated depression 32 in the surface of the second inclined surface 26 of the polygonal-shaped elevating member 16. The arcuate elongated depression 32 cradles and secures a lower portion of a recuperating leg 10.

The cantilever member 18 includes an elongated concave channel 34 fashioned near a lower portion of the cantilever member 18. The elongated concave channel 34 is grooved between the upper portion of the cantilever member 18 and a lower securing surface 36. As noted above, a hook and pile combination 38, such as that sold under the trademark VELCRO, comprises the surface of the securing surface 36 and releasably connects the securing surface 36 to the distal vertical end 40 of the polygonal-shaped elevating member 16.

The upper portion of the cantilever member 18 is connected with the polygonal-shaped elevating member 16 by said elastic straps 28 such that enhanced resistance is provided to a patient's foot 30. The inner surface 42 of each elastic strap 20, 22, and 28 is fitted with VELCRO on the outer edges. The outer surface 44 of elastic straps 20, 22, and 28 is not covered with VELCRO. One edge of the inner surface 432 of elastic strap 28 is engaged with the upper outer surface 46 of the cantilever member 18, and the other edge of the inner surface 42 of the elastic strap 28 is engaged with a lateral vertical side 48 of the polygonal-shaped elevating member 16, as illustrated in FIGS. 1 and 2.

The surface of the polygonal-shaped elevating member 16 is comprised of VELCRO on all sides except the arcuate elongated depression 32, the first inclined surface 24, and the bottom of the polygonal-shaped elevating member 16. The VELCRO allows attachment of elastic straps 20 and 22 across the upper and lower portions of a patient's leg 10. The elastic straps 20 and 22 may be secured to any position on the lateral sides 48 of the polygonal-shaped elevating member 16 to compensate for the varying leg size of a patient.

Referring particularly to FIG. 3, shown is the substantially homogeneous elastic foam composition 50 of the polygonal-shaped elevating member 16. The surface of the polygonal-shaped elevating member 16 is covered with VELCRO, except on the surface of the arcuate elongated groove 32. An outline of a patient's lower leg is shown secured to the second inclined surface 26 by elastic strap 22. Note that the inner surface 42 of elastic strap 22 is engaged by VELCRO with lateral sides 48 of the polygonal-shaped elevating member 16. The cantilever member 18 is also composed of a substantially homogeneous elastic foam (not shown).

As shown in FIG. 4, the resistance provided by the cantilever member 18 may be countered by dorsiflexion of a patient's foot 30 away from the body of a patient. The cantilever member 18 operably bends about the elongated concave channel 34, which acts as a hinge. The range of motion of the cantilever member 18 is a function of the force applied to the cantilever member 18 by the leg muscles of a patient.

FIG. 5 illustrates the self restoring characteristics of the composition of the therapeutic leg elevator 12. Note the conformity of the cantilever member 18 to the sole of a patient's foot 30. The distal end of the cantilever member 18 is shown flexing in response to pressure exerted by a patient's foot 30.

SUMMARY OF MAJOR ADVANTAGES OF THE INVENTION

After reading and understanding the foregoing inventive therapeutic leg elevator, in conjunction with the drawings, it will be appreciated that several distinct advantages of the subject invention are obtained.

Without attempting to set forth all of the desirable features of the instant therapeutic leg elevator, at least some of the major advantages of the invention include the novel configuration which allows for both elevation of a convalescent patient's leg and independent exercise of the leg muscles by the patient. The combination of these effects allows maximal enhancement of venous outflow from the lower portion of the leg, decreases the incidence of venous edema, and prevents venous stasis, as described above.

Elevation of a patient's knee above the hip by means of a first inclined surface 24, and accompanying elevation of a patient's foot above the knee by means of a second inclined surface 26, utilizes the passive force of gravity to facilitate venous outflow from the foot. The elongated arcuate groove 32 carved into the surface of the second inclined surface 26 comfortably cradles and stabilizes the lower portion of a patient's leg.

The cantilever member 18 provides resistance to the foot 30 of a patient which allows stimulation of the leg muscles and accompanying increased venous outflow. The elastic straps 20 and 22 allow adjustment of the resistance provided to a patient's foot 30. The elongated concave channel 34 provides a hinge about which the upper portion of the cantilever member 18 may bend, and is fashioned such that the heel of a patient's foot may comfortably extend below the plane of a second planar surface 26.

Use of elastic straps 20 and 22 with VELCRO allows secure yet adjustable connection of the inner surface 42 of elastic straps 20 and 22 to the lateral sides 48 of therapeutic leg elevator 12. Elastic straps 20 and 22 also secure a patient's leg 10 to the therapeutic leg elevator 12 while allowing for maximum exposure of a patient's leg 10 to the atmosphere. The covering of an entire lateral side 38 of the therapeutic leg elevator 12 with VELCRO allows varying attachment of the elastic straps 20 and 22 as dictated by the medical needs of a patient. The releasable nature of elastic straps 20 and 22 allows for facile neurovascular examination. The releasable engagement of the distal lateral side 40 of the polygonal-shaped elevating member 16 and the cantilever member 18 facilitates disassembly and reassembly of the therapeutic leg elevator 12, which is convenient when the therapeutic leg elevator 12 is being transported.

The homogeneous elastic foam composition of the therapeutic leg elevator 12 comfortably elevates and supports the recuperating leg 10 of a patient while having self restoring characteristics which make it suitable for use as a hinge by the cantilever member 18. Because of its foam composition, the therapeutic leg elevator 12 is easily manufactured, personalized to various sized patients, relatively inexpensive, and is disposable.

In describing the invention, reference has been made to a preferred embodiment and illustrative advantages of the invention. Those skilled in the art; however, and familiar with the instant disclosure of the subject invention, may recognize additions, deletions, modification, substitutions and/or other changes which will fall within the purview of the subject invention and claims.

What is claimed is:

1. A therapeutic leg elevator for use in promoting venous flow during patient recuperation comprising:
   means for underlying and supporting a lower portion of a patient's leg in an elevated position when a patient is in a supine recuperative posture, said means for underlying and supporting being,
   a substantially homogeneous solid polygonal-shaped member composed of elastic foam having external surfaces including,
   a first inclined surface for supporting a back portion of a patient's thigh, a second surface inclined with respect to said first inclined surface for supporting a patient's lower leg, a generally vertical distal end surface, two generally vertical lateral side surfaces, and a substantially flat bottom surface;

resistance means connected to a distal end of said means for underlying and supporting a lower portion of a patient's leg and being operable to be adjacent to a sole portion of a patient's foot to provide resistance exercise whereby a patient positioned in a supine recuperative posture may utilize foot flexion about an ankle joint and against said resistance means to promote lower limp venous flow during patient recuperation; and means for releasably connecting said resistance means to a distal end of said means for underlying and supporting, said means for releasably connecting being one of a hood and pile connecting combination connected to said means for underlying and supporting and the other of said hook and pile combination connected to said resistance means.

2. A therapeutic leg elevator as defined in claim 1 wherein:

said second inclined surface is an extension of said first inclined surface such that said second inclined surface in combination with said first inclined surface forms a double incline plan with respect to a horizontal surface such that a patient's ankle is supported in an elevated posture with respect to the patient's knee.

3. A therapeutic leg elevator as defined in claim 2 wherein:

said second inclined surface is fashioned with an elongated arcuate groove along said second inclined surface whereby said groove provides a cradle for receiving, restraining and supporting a patient's lower leg.

4. A therapeutic leg elevator as defined in claim 3 and further comprising:

an elastic strap operable to overlay a patient's upper leg and releasably connect to said lateral sides of said leg elevator whereby said patient's upper leg is retained in a stabilized posture.

5. A therapeutic leg elevator as defined in claim 4 and further comprising:

an elastic strap operable to overlay a patient's lower leg and releasably connect to said lateral sides of said leg elevator whereby said patient's lower leg is retained in a stabilized posture.

6. A therapeutic leg elevator as defined in claim 1 wherein said resistance means comprises:

a cantilever vertical member releasably connected by a hook and pile connecting combination to a distal end of said means for underlying and supporting a lower portion of a patient's leg.

7. A therapeutic leg elevator as defined in claim 6 wherein said cantilever vertical member comprises:

a substantially homogeneous elastic foam member having self restoring characteristics.

8. A therapeutic leg elevator as defined in claim 7 wherein said cantilever vertical member includes:

an elongated concave channel fashioned near a lower end of said cantilever vertical member whereby the concave channel operably serves as a hinge for said resistance means.

9. A therapeutic leg elevator as defined in claim 8 wherein said resistance means further comprises:

at least one elastic strap releasably connected between a free end of said cantilever vertical member and a lateral side of said solid polygonal-shaped member whereby said exercise strap when adjustably positioned provides means for compression of the muscles by plantar flexion of the foot.

10. A therapeutic leg elevator as defined in claim 9 wherein said at least one elastic strap comprises:

a pair of elastic straps one substantially adjacent a corner of said free end of said cantilever vertical member releasably connected to the lateral sides of said means for underlying and supporting and the edges of said cantilever member.

11. A therapeutic leg elevator for use in promoting venous flow during patient recuperation comprising:

means for underlying and supporting a lower portion of a patient's leg in an elevated position when a patient is in a supine recuperative posture, said means for underlying and supporting being, a substantially homogeneous solid polygonal-shaped member composed of elastic foam having external surfaces including, a first inclined surface for supporting a back portion of a patient's thigh, a second surface inclined with respect to said first inclined surface for supporting a patient's lower leg, a generally vertical distal end surface, two generally vertical lateral side surfaces, and a substantially flat bottom surface;

resistance means comprising a cantilever vertical member releasably connected to a distal end of said means for underlying and supporting a lower portion of a patient's leg and being operable to be adjacent to a sole portion of a patient's foot to provide resistance exercise whereby a patient positioned in a supine recuperative posture may utilize foot flexion about an ankle joint and against said resistance means to promote lower limb venous flow during patient recuperation, said resistance means having, an elongated concave channel fashioned near a lower end of said cantilever vertical member whereby the concave channel operably serves as a hinge for said resistance means; and means for releasably connecting said resistance means to a distal end of said means for underlying and supporting, said means for releasably connecting being one of a hook and pile connecting combination connected to said means for underlying and supporting and the other of said hook and pile combination connected to said resistance means.

12. A therapeutic leg elevator as defined in claim 11 wherein:

said second inclined surface is an extension of said first inclined surface such that said second inclined surface in combination with said first inclined surface forms a double inclined plane with respect to a horizontal surface such that a patient's ankle is supported in an elevated posture with respect to the patient's knee.

13. A therapeutic leg elevator as defined in claim 12 wherein:

said second inclined surface is fashioned with an elongated arcuate groove along said second inclined surface whereby said groove provides a cradle for receiving, restraining, and supporting a patient's lower leg.

14. A therapeutic leg elevator as defined in claim 13 and further comprising:

an elastic strap operable to overlay a patient's upper leg and releasably connect to said lateral sides of said leg elevator whereby said patient's upper leg is retained in a stabilized posture.

15. A therapeutic leg elevator as defined in claim 14 and further comprising:

an elastic strap operable to overlay a patient's upper leg and releasably connect to said lateral sides of said leg elevator whereby said patient's upper leg is retained in a stabilized posture.

16. A therapeutic leg elevator as defined in claim 11 wherein said cantilever vertical member comprises:

a substantially homogeneous elastic foam member having self restoring characteristics.

17. A therapeutic leg elevator as defined in claim 11 wherein said resistance means further comprises:

at least one elastic strap releasably connected between a free end of said cantilever vertical member and lateral side of said polygonal-shaped member.

18. A therapeutic leg elevator as defined in claim 17 wherein said at least one elastic strap comprises:

a pair of elastic straps, one substantially adjacent a corner of said free end of said vertical cantilever member, releasably connected to the lateral sides of said means for underlying and supporting and the edges of said cantilever member.

* * * * *